United States Patent
Morimoto et al.

(10) Patent No.: US 6,222,054 B1
(45) Date of Patent: Apr. 24, 2001

(54) METHOD FOR PRODUCING EPOXY RESIN

(75) Inventors: Takashi Morimoto; Hideshi Sakamoto, both of Niihama; Masakazu Takahashi, Kagawa, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/447,581

(22) Filed: Nov. 23, 1999

(30) Foreign Application Priority Data

Dec. 1, 1998 (JP) .................................................. 10-341877

(51) Int. Cl.⁷ ........................ C07D 301/30; C07D 301/28
(52) U.S. Cl. ............................................. 549/517; 549/516
(58) Field of Search ..................................... 549/516, 517

(56) References Cited

U.S. PATENT DOCUMENTS 4,390,664 * 6/1983 Kanayama ........................... 525/117
5,612,442 * 3/1997 Okazaki et al. ..................... 528/212
5,945,501 * 8/1999 Okazaki et al. ....................... 528/97

FOREIGN PATENT DOCUMENTS

| 53 087927 | 8/1978 | (JP) . |
| 53 127599 | 11/1978 | (JP) . |
| 57 073017 | 5/1982 | (JP) . |

* cited by examiner

*Primary Examiner*—Ba K. Trinh
(74) *Attorney, Agent, or Firm*—Sughrue, Mion, Zinn, Macpeak & Seas, PLLC

(57) ABSTRACT

The method for producing an epoxy resin involving the steps of: reacting at least one phenol compound with at least one aldehyde compound to obtain a novolak resin; storing the novolak resin in a molten state in an inert gas atmosphere; feeding the stored novolak resin into an epoxidation reactor; and reacting the stored novolak resin with an epihalohydrin compound, which prevents generation of dust improving the working environment, increases production efficiency reducing production cost, and further suppresses quality degradation such as coloring of the epoxy resin.

13 Claims, No Drawings

METHOD FOR PRODUCING EPOXY RESIN

BACKGROUND OF THE INVENTION

1. Field of the Invention

The present invention relates to a method for producing a novolak-type epoxy resin used for a encapsulating material and the like in the electric and electronic industries.

2. Description of the Related Art

In normal production of an o-cresol novolak-type epoxy resin, first, o-cresol is reacted with formalin to obtain an o-cresol novolak resin as an intermediate material. Then, the o-cresol novolak resin is fed into an epoxidation reactor together with epichlorohydrin and, if necessary, a solvent also, to allow for epoxidation. One of major factors for determining the properties or quality of the thus-produced epoxy resin is the molecular structure, in particular, skeleton structure of the novolak resin.

Whether or not a novolak resin has a desired molecular structure is normally determined by measuring the softening point of the resin. In other words, a novolak resin having a specific softening point is used for epoxidation so that an epoxy resin having a desired molecular structure or desired properties such as softening point, etc., can be produced.

Therefore, in order to produce an epoxy resin suitable for a desired usage, it is required to prepare a novolak resin having a predetermined softening point.

In a conventional production process of a novolak resin, a novolak resin produced in a reactor is once solidified by cooling into flakes to avoid possible quality degradation and the like. The resin flakes are stored in an appropriate container so that a required amount of the resin can be fed into a reactor when an epoxy resin is to be produced.

The above process has following problems. The operations of putting the novolak resin in a container and taking a predetermined amount of the resin out from the container to feed it into a reactor are mostly performed manually. Dust of the novolak resin generated during these operations may worsen the working environment.

Another problem is that the resultant epoxy resin is colored. In particular, when the novolak resin is stored at higher temperature than normal temperature as in summer, it may degrade by oxidation, causing quality degradation of the resultant epoxy resin such as significant coloring, an increase in epoxy equivalent weight, and a change in softening point.

The inventors have intensively studied for solving the above problems and found that the novolak resin can be prevented from quality degradation by storing it in a molten state in an inert gas atmosphere, and that this storage in a molten state allows for in-line handling of the resin, improving operability and the working environment.

SUMMARY OF THE INVENTION

Accordingly, it is an object of the present invention to provide a method for producing an epoxy resin where no manual operation is necessary in handling a novolak resin, no dust is generated, and the quality of the epoxy resin is stabilized.

Another object of the present invention is to provide a method for producing an epoxy resin capable of easily producing an epoxy resin having desired properties.

The present invention provides the method for producing an epoxy resin comprising the steps of: reacting at least one phenol compound with at least one aldehyde compound to obtain a novolak resin; storing the novolak resin in a molten state in an inert gas atmosphere; feeding the stored novolak resin into an epoxidation reactor; and reacting the novolak resin with an epihalohydrin compound.

The present invention also provides the method for producing an epoxy resin comprising the steps of: reacting separately at least one phenol compound with at least one aldehyde compound to obtain separately at least two novolak resins having different softening points; storing separately at least two novolak resins in the molten state in an inert gas atmosphere; feeding at least two stored novolak resins into an epoxidation reactor and mixing thereof; and reacting the mixed novolak resins with an epihalohydrin compound.

According to the method of the present invention, the novolak resin as an intermediate material is stored in a molten state in an inert gas atmosphere, without once being moved outside of vessels as solid flakes as in the conventional case, to allow for in-line feeding for epoxidation. This eliminates the necessity of manual operations such as transportation and feeding of the novolak resin, prevents generation of dust, and suppresses quality degradation of the epoxy resin caused by the novolak resin being exposed to the air in a high-temperature environment.

According to the present invention, it is preferable to store the plural novolak resins having different softening points separately in a molten state in an inert gas atmosphere. Further, the plural novolak resins having different softening points may be mixed, to react the mixture with an epihalohydrin compound for epoxidation.

This makes it possible to easily respond to production of various kinds of epoxy resins which are different in properties such as the softening point.

The reason why the softening point is used for separating a kind of novolak resin from another is that the softening point can be an index for the molecular structure of the novolak resin such as the molecular weight and the molecular weight distribution as previously described. Besides the softening point, other properties which can be such an index, such as the viscosity and the melting point, may also be used.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

In the step of reacting at least one phenol compound with at least one aldehyde compound to obtain a novolak resin, at least one phenol compound and an acid catalyst are fed into a reactor, and at least one aldehyde compound is added dropwise while heating to a predetermined temperature and stirring, for polymerization.

After the reaction is completed, the resultant solution is subjected to neutralization and other processing such as separation of an aqueous solution, and heated under atmospheric pressure or reduced pressure removing water and unreacted substances to obtain a novolak resin.

Examples of the phenol compound include phenol, o-cresol, m-cresol, p-cresol, resorcinol, brominated phenol, brominated cresol, brominated resorcinol, naphthol and the like.

Examples of the acid catalyst include p-toluene sulfonic acid, oxalic acid, sulfuric acid, hydrochloric acid and the like.

Examples of the aldehyde compound include formaldehyde, acetaldehyde, butyraldehyde, benzaldehyde and the like.

The degree of polymerization of the resultant novolak resin is normally 2 to about 20. The molecular structure [skeleton structure expressed with the average molecular weight (degree of condensation polymerization), the molecular weight distribution, the bonding form and the like] of the novolak resin can be controlled by adjusting the reaction conditions such as the molar ratio of at least one aldehyde compound to at least one phenol compound fed into the reactor, the drop rate of at least one aldehyde compound, the reaction time, the reaction temperature, and the amount of catalyst. The molar ratio of at least one aldehyde compound to at least one phenol compound is normally selected in the range of about 0.4 to 0.9.

In general, the softening point is used as an index for the molecular structure of the novolak resin. By adjusting the production conditions described above, various kinds of novolak resins having softening points normally in the range of room temperature to about 200° C. can be produced.

The resultant novolak resin is stored as it is in the same reactor or in a separate storage vessel in a molten state. When various kinds of novolak resins are produced, they are stored in separate storage vessels depending on their softening points.

According to the present invention, the molten novolak resin is stored in an inert gas atmosphere since it degrades in quality upon contact with oxygen. The type of the inert gas is not specifically limited as long as it is inert to a molten novolak resin. For example, nitrogen gas, helium gas, hydrogen gas, and the like may be used. Normally, nitrogen gas is used since it is economical and easy in handling.

The oxygen concentration of the inert gas is normally about 1000 ppm or less, preferably about 500 ppm or less, more preferably about 250 ppm or less. When nitrogen gas is used, it may be nitrogen gas for industrial use, not specifically purified one. The oxygen concentration of such nitrogen gas is normally about 1000 ppm or less.

Normally, the atmosphere in the vessel for storing the molten novolak resin is replaced by an inert gas. The molten novolak resin is then put in the vessel. The inert atmosphere is ensured by keeping the gas layer in association with an inert gas source to prevent the air from entering the vessel while the novolak resin is stored.

The storage vessel is provided with an appropriate heating means to allow the novolak resin to be stored in a molten state. If the heating temperature is too low, it is difficult to keep the novolak resin in an appropriate flow state. If it is excessively high, the chemical bond of the novolak resin may be cleaved or rearranged causing quality degradation. It is therefore preferable to store the novolak resin at the lowest temperature that ensures an appropriate flow state. Normally, such a temperature is appropriately adjusted higher than the softening point of the novolak resin by about 20 to 60° C., preferably by about 20 to 40° C., if the softening point is used as a reference. The pH of the novolak resin during storage also affects the quality of the novolak resin. In general, therefore, the pH is preferably adjusted in the range of about 6 to 9 during the storage of the novolak resin.

The storage vessel is preferably provided with a stirrer or a circulation device which circulates the novolak resin in the vessel so as to keep the novolak resin in a flow state. Such a circulation device, for example, enables the content of the vessel to exit from the vessel via a bottom port thereof and flow up to an upper port of the vessel by means of a circulation pump to return to the inside of the vessel.

The storage period of the novolak resin is preferably short. In general, it is preferably within two weeks, further preferably within one week. For example, when an o-cresol novolak resin having a softening point of about 90° C. is stored at 120° C., no significant change in properties is recognized if the storage period is two or three weeks.

In the steps of feeding the stored novolak resin into an epoxidation reactor, a novolak resin having a desired softening point is taken out from the storage vessel and dissolved in an organic solvent together with an epihalohydrin compound.

Examples of the epihalohydrin compound include epichlorohydrin and epibromhydrin. The epihalohydrin compound is used in an amount of moles twice to fifteen times as much as those of the phenol hydroxyl group of the novolak resin.

Examples of the organic solvent include ketones such as methylethylketone and methylisobutylketone, hydrocarbons such as toluene and xylene, alcohols such as methanol and ethanol, cellosolves such as methylcellosolve and ethylcellosolve, ethers such as dioxane and diethoxyethane, dimethylsulfoxide and dimethylformamide.

In the step of reacting the novolak resin with an epihalohydrin, the solution obtained by mixing and dissolving as described above is then epoxidated by a normal method. More specifically, an aqueous solution of caustic alkali having an equivalent of about 0.9 to 1.1 to the phenol hydroxyl group of the novolak resin is gradually added to the novolak resin solution under atmospheric pressure or reduced pressure at a temperature of about 30 to 100° C. for epoxidation. During this reaction, azeotropic dehydration is preferably performed for controlling the water content in the system.

Examples of the caustic alkali include potassium hydroxide and sodium hydroxide. Such caustic alkali is normally added in the form of about 20 to 55% by weight aqueous solution.

The epoxidation may be performed in one stage or two stages.

After the epoxidation is completed, an excess of the epihalohydrin and the solvent are removed and salt and the like produced are removed to obtain an epoxy resin.

In order to produce an epoxy resin having a desired softening point, viscosity, molecular weight distribution, or the like, the novolak resin used as an intermediate material should have a predetermined softening point. If a plurality of kinds of novolak resins having different softening points are producing separately and stored separately in a molten state as described above, it is possible to prepare a novolak resin having a desired softening point by mixing two or more kinds among the stored novolak resins. For example, when W parts by weight of novolak resin A having a softening point $T_A$ and (1−W) parts by weight of novolak resin B having a softening point $T_B$ (W denotes the mixing weight ratio of novolak resin A with respect to novolak resin B) are mixed to obtain 1 part by weight of novolak resin C having a softening point $T_C$, the relationship represented by the equation (1) below is satisfied.

$$T_A \times W + T_B \times (1-W) = T_C \tag{1}$$

From the equation (1), therefore, the mixing amount W of novolak resin A and thus the mixing amount (1−W) of novolak resin B can be obtained.

Normally, the difference in softening point between the plural novolak resins to be mixed is preferably about 30° C. or less. That is, if the plural novolak resins having softening points which are different by about 30° C. or less are mixed to be used as an intermediate material for the production of an epoxy resin, the resultant epoxy resin possesses properties, such as the softening point, the viscosity, and the molecular weight distribution, which are not so largely different from those obtained when a single novolak resin having the same softening point as the mixture is used.

As a criterion for mixing the plural novolak resins having different softening points, the blend coefficient represented by the equation (2) below is also preferably adopted. The blend coefficient is preferably about 10 or less in order to obtain a novolak resin having a desired softening point. The equation (2) represents a general expression to be used for the case where i kinds of novolak resins are to be mixed.

$$\text{Blend coefficient} = \frac{\sum_{1}^{i} (|S_n - S_x| \times V_n / V_t)}{S_x} \times 100 \quad (2)$$

wherein $S_n$ denotes the softening point of the n-th novolak resin, $S_x$ denotes a mean softening point of the novolak resins (equal to the softening point $T_C$ of the mixed novolak resin described above), $V_n$ denotes the weight of the n-th novolak resin, and $V_t$ denotes the total weight of the novolak resins.

The chemical structures of the novolak resins to be mixed together, which is changed with phenol compounds and/or aldehyde compounds used, may be of the same type or may be different.

EXAMPLES

The method for producing an epoxy resin of the present invention will be illustrated in greater detail with reference to the following examples and comparative examples.

The resin obtained in each of the following examples was evaluated using the following method.

(1) Softening Point

Measured by the ball-and-ring method using an automatic softening point measuring apparatus (EX-820 manufactured by Elec Science Co., Ltd.)

(2) Kinematic Viscosity

A 1,4-dioxane solution containing 50% by weight of each resin sample was prepared, and the viscosity of the solution was measured at 25° C. using Canon Fenske viscometer (No.200, No.300).

(3) GPC Dispersion Ratio

Each resin sample was dissolved in tetrahydrofuran, and the GPC dispersion ratio was determined using the tetrahydrofuran as a carrier and two pieces of Plegel-MIXED-E (product name) manufactured by Polymer Laboratory Co. as columns.

(4) pH of a Resin

Two grams of a resin sample were dissolved in 40g of chloroform, and 40g of pure water was added to the solution and mixed sufficiently. The resultant solution was allowed to stand to separate itself, and the pH of a water layer was measured by a pH meter.

(5) Epoxy Equivalent Weight

A dioxane solution of 0.1N hydrochloric acid was added to each resin sample and allowed to react while stirring for 15 minutes. The resultant solution was subjected to potential difference titration with a methanol solution of 0.1N sodium hydroxide, so as to calculate the equivalent of the epoxy group which had reacted with the hydrochloric acid based on the difference between the measured titer and the titer of a blank. The epoxy equivalent weight (g/eq) was obtained by dividing the sample amount by the calculated equivalent.

(6) Color of a Resin

The color of a resin was evaluated by Gardner Number (G-No.).

Example 1

(Production and Storage of Novolak Resin)

To 100 parts by weight of o-cresol were added 67.6 parts by weight of 37% formalin, and the mixture was left for reaction for 6 hours at 103° C. using 1.2 parts by weight of p-toluene sulfonic acid as a catalyst. After the reaction solution was neutralized with sodium hydroxide, 49.2 parts by weight of water was added, and water soluble impurities were removed by separation. After the resultant solution was concentrated under reduced pressure at 155° C., the o-cresol novolak resin was obtained.

The resultant o-cresol novolak resin had a softening point of 125.6° C. Hereinafter, this o-cresol novolak resin is referred to as Resin A.

Resin A was put in a storage vessel provided with a stirrer and a circulation pump connected with a bottom port of the vessel, and stored in the vessel in a molten state at 160° C. in an atmosphere of nitrogen gas for industrial use.

Example 2

(Production and Storage of Novolak Resin)

To 100 parts by weight of o-cresol were added 61.5 parts by weight of 37% formalin, and the mixture was left for reaction for 5 hours at 103° C. using 1.2 parts by weight of p-toluene sulfonic acid as a catalyst. After the reaction solution was neutralized with sodium hydroxide, 49 parts by weight of water was added, and water soluble impurities were removed by separation. After the resultant solution was concentrated under reduced pressure at 160° C., the resultant o-cresol novolak resin was obtained.

The resultant o-cresol novolak resin had a softening point of 104.5° C. Hereinafter, this o-cresol novolak resin is referred to as Resin B.

Resin B was put in a storage vessel provided with a stirrer and a circulation pump connected with a bottom port of the vessel, and stored in the vessel in a molten state at 140° C. in an atmosphere of nitrogen gas for industrial use.

Example 3

(Production and Storage of Novolak Resin)

To 100 parts by weight of o-cresol were added 56.9 parts by weight of 37% formalin, and the mixture was left for reaction for 4 hours at 103° C. using 0.7 parts by weight of p-toluene sulfonic acid as a catalyst. After the reaction solution was neutralized with sodium hydroxide, 46.8 parts by weight of water was added, and water soluble impurities were removed by separation. After the resultant solution was concentrated under reduced pressure at 160° C., the o-cresol novolak resin was obtained.

The resultant o-cresol novolak resin had a softening point of 89.3° C. Hereinafter, this o-cresol novolak resin is referred to as Resin C.

Resin C was put in a storage vessel provided with a stirrer and a circulation pump connected with a bottom port of the vessel, and stored in the vessel in a molten state at 130° C. in an atmosphere of nitrogen gas for industrial use.

Comparative Example 1

(Production and Storage of Novolak Resin)

To 100 parts by weight of o-cresol were added 62 parts by weight of 37% formalin, and the mixture was left for reaction for 5 hours at 103° C. using 1.2 parts by weight of p-toluene sulfonic acid as a catalyst. After the reaction solution was neutralized with sodium hydroxide, 49.0 parts by weight of water was added, and water soluble impurities were removed by separation. After the resultant solution was concentrated under reduced pressure at 160° C., the o-cresol novolak resin was obtained.

The resultant o-cresol novolak resin had a softening point of 109.7° C. Hereinafter, this o-cresol novolak resin is referred to as Resin D.

Resin D was rolled and cooled, and stored as flakes in a container.

Comparative Example 2
(Production and Storage of Novolak Resin)

To 100 parts by weight of o-cresol were added 60.5 parts by weight of 37% formalin, and the mixture was left for reaction for 5 hours at 103° C. using 1.2 parts by weight of p-toluene sulfonic acid as a catalyst. After the reaction solution was neutralized with sodium hydroxide, 49.0 parts by weight of water was added, and water soluble impurities were removed by separation. After the resultant solution was concentrated under reduced pressure at 160° C., the o-cresol novolak resin was obtained.

The resultant o-cresol novolak resin had a softening point of 99.30C. Hereinafter, this o-cresol novolak resin is referred to as Resin E.

Resin E was rolled and cooled, and stored as flakes in a container.

Example 4
(Production of Epoxy Resin)

Resin A and B were mixed at a weight ratio of 0.246 0.754 for A:B (the blend coefficient mentioned above was 7.14) so that the softening point of the mixture be 109.7° C. To 100 parts by weight of the mixed o-cresol novolak resin were added 539.6 parts by weight of epichlorohydrin and 188.8 parts by weight of 1,4-dioxane. Then, 19.4 parts by weight of a 48% potassium hydroxide aqueous solution were added dropwise over one hour under a reduced pressure of 8000 Pa (60 torr) at 39° C., and the resultant solution was aged for 3.5 hours under the same conditions. During the aging, liquid distillates were removed using a separation pot while oil distillates were returned to the system.

After the reaction system was adjusted to the conditions of 20000 Pa (150 torr) and 60° C., 53.5 parts by weight of 48% sodium hydroxide were added dropwise over 3.5 hours. During this dropping, also, water distillates were removed.

After the completion of the reaction, an excess of epichlorohydrin and 1,4-dioxane were distilled off. Methylisobutylketone was added to the residue, and by-product sodium chloride was removed by washing and filtration. Finally, methylisobutylketone was distilled off to obtain an o-cresol novolak-type epoxy resin.

The evaluation results are shown in Table 1 below.

Example 5
(Production of Epoxy Resin)

In this example, Resin B and C were mixed at a weight ratio of 0.658:0.342 for B:C (the blend coefficient was 6.89) so that the softening point of the mixture be 99.3° C., and the mixed o-cresol novolak resin, 100 parts by weight, was used. The other steps for producing an o-cresol novolak-type epoxy resin of this example were the same as those described in Example 4.

The evaluation results are shown in Table 1 below.

Comparative Example 3
(Production of Epoxy Resin)

To 100 parts by weight of Resin D having a softening point of 109.7° C., 539.6 parts by weight of epichlorohydrin and 188.8 parts by weight of 1,4-dioxane were added. Then, 19.4 parts by weight of a 48% potassium hydroxide aqueous solution were added dropwise over one hour under a reduced pressure of 8000 Pa (60 torr) at 39° C., and the resultant solution was aged for 3.5 hours under the same conditions. During the aging, liquid distillates were removed using a separation pot while oil distillates were returned to the system. After the reaction system was adjusted to the conditions of 20000 Pa (150 torr) and 60° C., 53.5 parts by weight of 48% sodium hydroxide were added dropwise over 3.5 hours. During this dropping, also, water distillates were removed.

After the completion of the reaction, an excess of epichlorohydrin and 1,4-dioxane were distilled off. Methylisobutylketone was added to the residue, and by-product sodium chloride was removed by washing and filtration. Finally, methylisobutylketone was distilled off to obtain an o-cresol novolak-type epoxy resin.

The evaluation results are shown in Table 1 below.

Comparative Example 4
(Production of Epoxy Resin)

An o-cresol novolak-type epoxy resin of this comparative example was produced in the same process as that described in Comparative Example 3 except that 100 parts by weight of Resin E having a softening point of 99.3° C. was used in place of Resin D.

The evaluation results are shown in Table 1 below.

TABLE 1

| | Novolak resin Softening point (° C.) | Epoxy resin | | |
| --- | --- | --- | --- | --- |
| | | Softening point (° C.) | Kinematic viscosity (cst) | GPC dispersion ratio |
| Example 4 | 109.7 (A:B = 0.246:0.754) | 78.8 | 76.7 | 2.12 |
| Example 5 | 99.3 (B:C = 0.658:0.342) | 71.9 | 63.3 | 1.97 |
| Comparative example 3 | 109.7 | 79.4 | 76.8 | 2.15 |
| Comparative example 4 | 99.3 | 71.3 | 62.5 | 1.96 |

From Table 1, it is observed that, in Example 4 where Resin A and B were mixed so as to have the same softening point as Resin D used as the starting material in Comparative Example 3, the softening point, kinematic viscosity, and GPC dispersion ratio of the resultant epoxy resin are almost the same as those of the epoxy resin in Comparative Example 3. This also applies to the combination of Example 5 and Comparative Example 4.

The above results indicate that a desired epoxy resin can be easily produced by using a mixture of the plural molten novolak resins having different softening points as a material for the production of the epoxy resin.

Example 6
(Production of Epoxy Resin)

An o-cresol novolak resin having a pH of 6.7 and a softening point of 96.7° C. was produced in the same process as that described in Example 3 except that the amount of the 37% formalin was changed to 58.7 parts by weight.

A portion of the resultant novolak resin was put in a vessel the inside of which had been adjusted at 120° C. in a nitrogen gas atmosphere, and stored therein in a molten state while stirring for 18 days. Using the stored novolak resin, an epoxy resin was produced in the manner described in Example 4.

The evaluation results are shown in Table 2-1 and 2-2 below.

Comparative Example 5
(Production of Epoxy Resin)

The remainder of the novolak resin obtained in Example 6 was spread over a butt and cooled to be solidified. The resultant resin was stored in a cool and dark place under contact with an atmosphere at an average temperature of 15° C. for the same period of time as in Example 6, i.e., 18 days. Then, using the stored novolak resin, an epoxy resin was produced in the manner described in Example 4.

The evaluation results are shown in Table 2-1 and 2-2 below.

Comparative Example 6
(Production of Epoxy Resin)

An epoxy resin was produced in the same process as that described in Comparative Example 5 except that the cooling solidified novolak resin was stored in an air-circulation type constant-temperature vessel set at 50° C. for 14 days.

The evaluation results are shown in Table 2-1 and 2-2 below.

TABLE 2-1

| | Novolak resin | | | |
|---|---|---|---|---|
| | Storage temperature (° C.) | Atmosphere | Storage period (day) | Softening point after storage (° C.) |
| Example 6 | 120 | Nitrogen gas | 18 | 95.8 |
| Comparative example 5 | 15 | Air | 18 | 96.5 |
| Comparative example 6 | 50 | Air | 14 | 95.4 |

TABLE 2-2

| | Epoxy resin | | |
|---|---|---|---|
| | Epoxy equivalent weight (g/eq) | Softening point (° C.) | Color (G-No.) |
| Example 6 | 194 | 63.5 | 1 |
| Comparative example 5 | 195 | 63.0 | 1 |
| Comparative example 6 | 204 | 62.4 | 8 |

From Table 2-1 and 2-2, it is found that, when a novolak resin is stored in a solid state in contact with the air under the condition of a possible rise of the storage temperature as in summer (Comparative Example 6), it degrades by oxidation causing an increase in epoxy equivalent weight, a decrease in softening point, coloring of the epoxy resin, significantly degrading the quality of the epoxy resin.

On the contrary, in Example 6 where the novolak resin was stored in a molten state at 120° C. in an atmosphere of nitrogen gas, degradation as described above was hardly observed.

Examples 7 and 8
(Production of Epoxy Resin)

An o-cresol novolak resin was produced in the same process as that described in Example 3 except that the neutralization with sodium hydroxide was adjusted so that the pH of the novolak resin be 8. The resultant novolak resin was stored in a molten state in an atmosphere of nitrogen gas in two separate vessels at temperatures of 120° C. and 150° C. while stirring. The respective stored resins were examined for temporal change after 10 days and 20 days.

The evaluation results are shown in Table 3 below.

TABLE 3

| | Properties of novolak resin | | | |
|---|---|---|---|---|
| | Storage temperature (° C.) | Softening point immediately after production (° C.) | Softening point after 10 day storage (° C.) | Softening point after 20 day storage (° C.) |
| Example 7 | 120 | 89.3 | 90.6 | 89.8 |
| Example 8 | 150 | 89.3 | 91.5 | 92.1 |

As is apparent from Table 3, no change was observed in the softening points of the novolak resins stored at temperatures of 120° C. and 150° C. compared with that obtained immediately after production (0 day storage).

Using the novolak resins stored for 10 days and 20 days at 120° C. and 150° C., respectively, epoxy resins were produced in the manner described in Example 4.

A reference epoxy resin was also produced using a novolak resin obtained immediately after production. The epoxy equivalent weight and softening point of each of the epoxy resins were measured.

The evaluation results are shown in Table 4 below.

TABLE 4

| | Properties of epoxy resin | | | | | |
|---|---|---|---|---|---|---|
| | Immediately after production | | After 10 day storage | | After 20 day storage | |
| | Epoxy equivalent (g/eq) | Softening point (° C.) | Epoxy equivalent (g/eq) | Softening point (° C.) | Epoxy equivalent (g/eq) | Softening point (° C.) |
| Example 7 | 195 | 58.4 | 195 | 58.2 | 194 | 58.5 |
| Example 8 | 195 | 58.4 | 195 | 57.9 | 195 | 59.7 |

From Tables 3 and 4, it is found that, in order to enhance the thermal stability during the storage of a novolak resin and produce an epoxy resin having substantially the same quality as the reference, the pH of the stored novolak resin should appropriately be adjusted to the range of about 6 to 9 and the storage temperature be set at a temperature higher than the softening point of the novolak resin by about 20 to 60° C., preferably by about 20 to 40° C.

Example 9 and Comparative example 7
(Storage of Novolak Resin)

The novolak resin produced in the same process as that described in Example 2 was stored in a molten state at 125° C. in a nitrogen gas atmosphere and an air atmosphere separately for 7 days while stirring. As a result, the portion stored in an air atmosphere exhibited significant coloring. The color of this resin was evaluated by Gardner Number and found to be 7 as compared with 1 for the portion stored in a nitrogen gas atmosphere.

Thus, according to the present invention, the novolak resin as an intermediate material is stored in a molten state, not in the conventional solid state, so that it can be fed in-line for epoxidation.

This prevents generation of dust improving the working environment, increases production efficiency reducing production cost, and further suppresses quality degradation such as coloring of the epoxy resin caused by the novolak resin being exposed to the air in a high-temperature environment.

When the plural novolak resins having different softening points are stored separately in a molten state, they can be mixed to easily produce various kinds of epoxy resins having different properties.

The invention being thus described, it will be obvious that the same may be varied in many ways. Such variations are not to be regarded as a departure from the sprit and scope of the invention, and such modifications as would be obvious to one skilled in the art are intended to be included within the scope of the following claims.

What is claimed is:

1. A method for producing an epoxy resin comprising the steps of:
   (a) reacting at least one phenol compound with at least one aldehyde compound to obtain a novolak resin;
   (b) storing said novolak resin in the molten state in an inert gas atmosphere;
   (c) feeding said stored novolak resin into an epoxidation reactor; and
   (d) reacting the novolak resin with an epihalohydrin compound.

2. A method for producing an epoxy resin comprising the steps of:
   (a) separately obtaining at least two novolak resins having, different softening points by reacting at least one phenol compound with at least one aldehyde compound to obtain a first novolak resin, and, separately reacting at least one phenol compound with at least one aldehyde compound to obtain a second novolak resin having a softening point different from the first novolak resin;
   (b) storing separately said at least two novolak resins in the molten state in an inert gas atmosphere;
   (c) feeding said at least two stored novolak resins into an epoxidation reactor and mixing thereof; and
   (d) reacting said mixed novolak resins with an epihalohydrin compound.

3. A method for producing an epoxy resin according to claim 1, wherein the novolak resin is stored in a storage vessel.

4. A method for producing an epoxy resin according to claim 1, wherein the novolak resin is stored in a reactor for producing the novolak resin.

5. A method for producing an epoxy resin according to claims 1 or 2, wherein the inert gas is nitrogen gas.

6. A method for producing an epoxy resin according to claims 1 or 2, wherein the inert gas has an oxygen concentration of 1000 ppm or less.

7. A method for producing an epoxy resin according to claim 1, wherein the novolak resin is adjusted to and stored at a pH in a range of 6 to 9.

8. A method for producing an epoxy resin according to claim 1, wherein the novolak resin is stored at a temperature higher than the softening point of the novolak resin by about 20 to 60° C.

9. A method for producing an epoxy resin according to claims 1 or 2, wherein the phenol compound is o-cresol and the aldehyde compound is formaldehyde.

10. A method for producing an epoxy resin according to claims 1 or 2, wherein the phenol compound is o-cresol, the aldehyde compound is formaldehyde and the epihalohydrin compound is epichlorohydrin.

11. A method for producing an epoxy resin according to claim 2, wherein each novolak resin is separately stored in a storage vessel.

12. A method for producing an epoxy resin according to claim 2, wherein each novolak resin is adjusted to and stored at a pH in a range of 6 to 9.

13. A method for producing an epoxy resin according to claim 2, wherein each novolak resin is stored at a temperature higher than its softening point by about 20 to 60° C.

* * * * *